United States Patent [19]

Lin et al.

[11] Patent Number: 4,677,197
[45] Date of Patent: Jun. 30, 1987

[54] PURIFICATION METHOD FOR TUMOR NECROSIS FACTOR

[75] Inventors: Leo S. Lin, Fremont; Ralph Yamamoto, San Francisco, both of Calif.

[73] Assignee: Cetus Corporation, Emeryville, Calif.

[21] Appl. No.: 792,815

[22] Filed: Oct. 30, 1985

[51] Int. Cl.⁴ ............................................. C07K 3/20
[52] U.S. Cl. .................................. 530/417; 530/351; 530/416; 435/68
[58] Field of Search ...................... 260/112 R; 435/68; 530/351, 412, 416, 417

[56] References Cited

U.S. PATENT DOCUMENTS

| | | | |
|---|---|---|---|
| 4,289,690 | 9/1981 | Pestka et al. | 260/112 R |
| 4,309,418 | 1/1982 | Green | 260/112 R |
| 4,495,282 | 1/1985 | Ohnishi et al. | 435/68 |

FOREIGN PATENT DOCUMENTS

| | | |
|---|---|---|
| 131789 | 1/1985 | European Pat. Off. |
| 0148311 | 7/1985 | European Pat. Off. |
| 155549 | 9/1985 | European Pat. Off. |
| 158286 | 10/1985 | European Pat. Off. |
| 168214 | 1/1986 | European Pat. Off. |
| 8603751 | 7/1986 | PCT Int'l Appl. |
| 2106117 | 4/1983 | United Kingdom. |

OTHER PUBLICATIONS

Shirai et al., "Cloning and Expression in *E. Coli* . . . TNF", *Nature* 313 1985, p. 803.
Wang et al., "Molecular Cloning of the Complementary DNA for h-TNF", *Science*, vol. 228, 1985, p. 149.
Pennica et al., "Human Tumour Necrosis Factor", *Nature* 312 (5996) 1985, p. 724.
Abe et al., "Purification of Rabbit Tumor Necrosis Factor", *FEB*, 1985, vol. 180(2), pp. 203-206.
Williamson et al., *PNAS*, 80, 5397-5401 (1983).

*Primary Examiner*—Maurice J. Welsh
*Assistant Examiner*—Garnette D. Draper
*Attorney, Agent, or Firm*—Janet E. Hasak; Elliott L. Fineman; Kate H. Murashige

[57] ABSTRACT

An improved method for purifying TNF, especially recombinantly produced TNF in bacteria, is disclosed. The purification employs a hydrophobic support in a chromatographic column which is then developed, preferably by HPLC. Preliminary purifications using anion exchange resins are also helpful.

12 Claims, 4 Drawing Figures

```
                                                    METSerThrGluSerMETIleArgAspValGluLeu
 121 GGCCGAGGAGGCGCTCCCCAAGAAGACAGGGGGGCCCCAGGGCTCCAGGCGGTGCTTGTT
     AlaGluGluAlaLeuProLysLysThrGlyGlyProGlnGlySerArgArgCysLeuPhe

181 CCTCAGCCTCTTCTCCTTCCTGATCGTGGCAGGCGCCACCACGCTCTTCTGCCTGCTGCA
     LeuSerLeuPheSerPheLeuIleValAlaGlyAlaThrThrLeuPheCysLeuLeuHis

241 CTTTGGAGTGATCGGCCCCCAGAGGGAAGAGTCCCCCAGGGACCTCTCTCTAATCAGCCC
     PheGlyValIleGlyProGlnArgGluGluSerProArgAspLeuSerLeuIleSerPro

301 TCTGGCCCAGGCAGTCAGATCATCTTCTCGAACCCCGAGTGACAAGCCTGTAGCCCATGT
     LeuAlaGlnAlaValArgSerSerSerArgThrProSerAspLysProValAlaHisVal
                    1          6          11         16
 361 TGTAGCAAACCCTCAAGCTGAGGGGCAGCTCCAGTGGCTGAACCGCCGGGCCAATGCCCT
     ValAlaAsnProGlnAlaGluGlyGlnLeuGlnTrpLeuAsnArgArgAlaAsnAlaLeu
          21         26         31         36
 421 CCTGGCCAATGGCGTGGAGCTGAGAGATAACCAGCTGGTGGTGCCCATCAGAGGGCCTGTA
     LeuAlaAsnGlyValGluLeuArgAspAsnGlnLeuValValProSerGluGlyLeuTyr
          41         46         51         56
 481 CCTCATCTACTCCCAGGTCCTCTTCAAGGGCCAAGGCTGCCCCTCCACCCATGTGCTCCT
     LeuIleTyrSerGlnValLeuPheLysGlyGlnGlyCysProSerThrHisValLeuLeu
          61         66         71         76
 541 CACCCACACCATCAGCCGCATCGCCGTCTCCTACCAGACCAAGGTCAACCTCCTCTCTGC
     ThrHisThrIleSerArgIleAlaValSerTyrGlnThrLysValAsnLeuLeuSerAla
          81         86         91         96
 601 CATCAAGAGCCCCTGCCAGAGGGAGACCCCAGAGGGGGCTGAGGCCAAGCCCTGGTATGA
     IleLysSerProCysGlnArgGluThrProGluGlyAlaGluAlaLysProTrpTyrGlu
          101        106        111        116
 661 GCCCATCTATCTGGGAGGGGTCTTCCAGCTGGAGAAGGGTGACCGACTCAGCGCTGAGAT
     ProIleTyrLeuGlyGlyValPheGlnLeuGluLysGlyAspArgLeuSerAlaGluIle
          121        126        131        136
 721 CAATCGGCCCGACTATCTCGACTTTGCCGAGTCTGGGCAGGTCTACTTTGGGATCATTGC
     AsnArgProAspTyrLeuAspPheAlaGluSerGlyGlnValTyrPheGlyIleIleAla
          141        146        151        156
 781 CCTGTGAGGAGGACGAACATCCAACCTTCCCAAACGCCTCCCCTGCCCCAATCCCTTTAT
     Leu...

841 TACCCCCTCCTTCAGACACCCTCAACCTCTTCTGGCTCAAAAAGAGAATTGGGGGCTTAG

901 GGTCGGAACCCAAGCTTAGAACTTTAAGCAACAAGACCACCACTTCGAAACCTGGGATTC

961 AGGAATGTGTGGCCTGCACAGTGAAGTGCTGGCAACCACTAAGAATTCAAACTGGGGCCT

1021 CCAGAACTCACTGGGGCCTACAGCTTTGATCCCTGACATCTGGAATCTGGAGACCAGGGA

1081 GCCTTTGGTTCTGGCCAGAATGCTGCAGGACTTGAGAAGACCTCACCTAGAAATTGACAC

1141 AAGTGGACCTTAGGCCTTCCTCTCTCCAGATGTTTCCAGACTTCCTTGAGACACGGAGCC

1201 CAGCCCTCCCCATGGAGCCAGCTCCCTCTATTTATGTTTGCACTTGTGATTATTTATTAT

1261 TTATTTATTATTTATTTATTTACAGATGAATGTATTTATTTGGGAGACCGGGGTATCCTG

1321 GGGGACCCAATGTAGGAGCTGCCTTGGCTCAGACATGTTTTCCGTGAAAACGGAGGCTGA

1381 ACAATAGGCTGTTCCCATGTAGCCCCCTGGCCTCTGTGCCTTCTTTTGATTATGTTTTTT

1441 AAAATATTATCTGATTAAGTTGTCTAAACAATGCTGATTTGGTGACCAACTGTCACTCAT

1501 TGCTGAGGCCTCTGCTCCCCAGGGAGTTGTGTCTGTAATCGGCCTACTATTCAGTGGCGA

1561 GAAATAAAGGTTGCTTAGGAAAGAA
```

FIG. 4

PURIFICATION METHOD FOR TUMOR NECROSIS FACTOR

TECHNICAL FIELD

The invention relates to the purification of desired proteins, in particular, recombinantly produced proteins. More specifically, the invention relates to purification of tumor necrosis factor (TNF) from the cellular extract or the medium of recombinant host cells. The method is also useful in purifying TNF from native sources.

BACKGROUND ART

The variations on the theme of protein purification have been explored for more than fifty years. The literature on this subject is extensive and a plethora of techniques is available to the practitioner, including ion exchange chromatography, adsorption chromatography, gel electrophoresis, ammonium sulfate precipitations, and gel filtration. Over the years there have been substantial improvements in the technology of conducting many of the foregoing methods, and in particular, it has been possible to automate and speed up the procedures related to column chromatography and development of electrophoresis gels. Despite these technical advances, and despite the large number of proteins which have been subjected to these procedures, the selection of a successful procedure, or more usually combination of procedures, for a particular protein found in a particular milieu has remained unpredictable, unselectable in advance, and subject to considerable experimentation in each particular case.

Human TNF has been purified as a native protein using culture supernatants from induced HL-60 cells as a source by a combination of anion exchange chromatography and reverse phase HPLC, with elution in a linear gradient of acetonitrile (Wang, A. M., et al *Science* (1985) 228: 149–154). Similar procedures had been previously employed (Matthews, N., *Br J Cancer* (1981) 44: 418) without resulting in a homogeneous preparation. However, this technique is not optimally efficient even for the native TNF secreted from, for example, HL-60 or other TNF secreting cell lines, and is inappropriate for recombinantly produced TNF, due to inactivation of biological activity at low pH.

The method of the invention substitutes a hydrophobic chromatographic support for the reverse phase support used previously and permits isolation of pure TNF and various TNF muteins using a decreasing salt concentration gradient. The resulting purified TNF is homogeneous with respect to TNF molecular size but, depending on the particular form of recombinant TNF produced, may contain side chain modifications detectable upon isoelectric focusing or other modifications which alter the isoelectric points.

DISCLOSURE OF THE INVENTION

The invention provides an improved method for purifying TNF, especially recombinant forms of TNF produced in bacterial hosts. The TNF thus produced may be substantially similar to the mature form or may contain deliberate or fortuitous amino acid modifications including N-terminal sequence deletions. The method of the invention produces TNF which is homogeneous on SDS-PAGE and which can thus be conveniently assessed for side chain modifications or other modifications using isoelectric focusing techniques.

In one aspect, the invention relates to a method to purify TNF by chromatography which comprises treating a mixture containing TNF in aqueous solution under high salt concentration conditions with a hydrophobic chromatographic support. Under these conditions, typically using a buffer containing approximately 1.5–2M ammonium sulfate or its equivalent in ionic strenght, the TNF and small quantities of other proteins are adsorbed to the hydrophobic support. The adsorbed protein is then eluted from the support by decreasing the concentration of salt, preferably in a continuous, but permissibly in a stepwise, gradient, to effect the elution of the TNF. This procedure results in clean separation of the TNF from any contaminating proteins.

In another aspect, the invention is directed to TNF prepared using the method of the invention.

BRIEF DESCRIPTION OF THE DRAWINGS

FIG. 4 shows the DNA sequence and deduced amino acid sequence of the cDNA encoding recombinantly produced human TNF.

MODES OF CARRYING OUT THE INVENTION

A. Definitions

Figure 1:
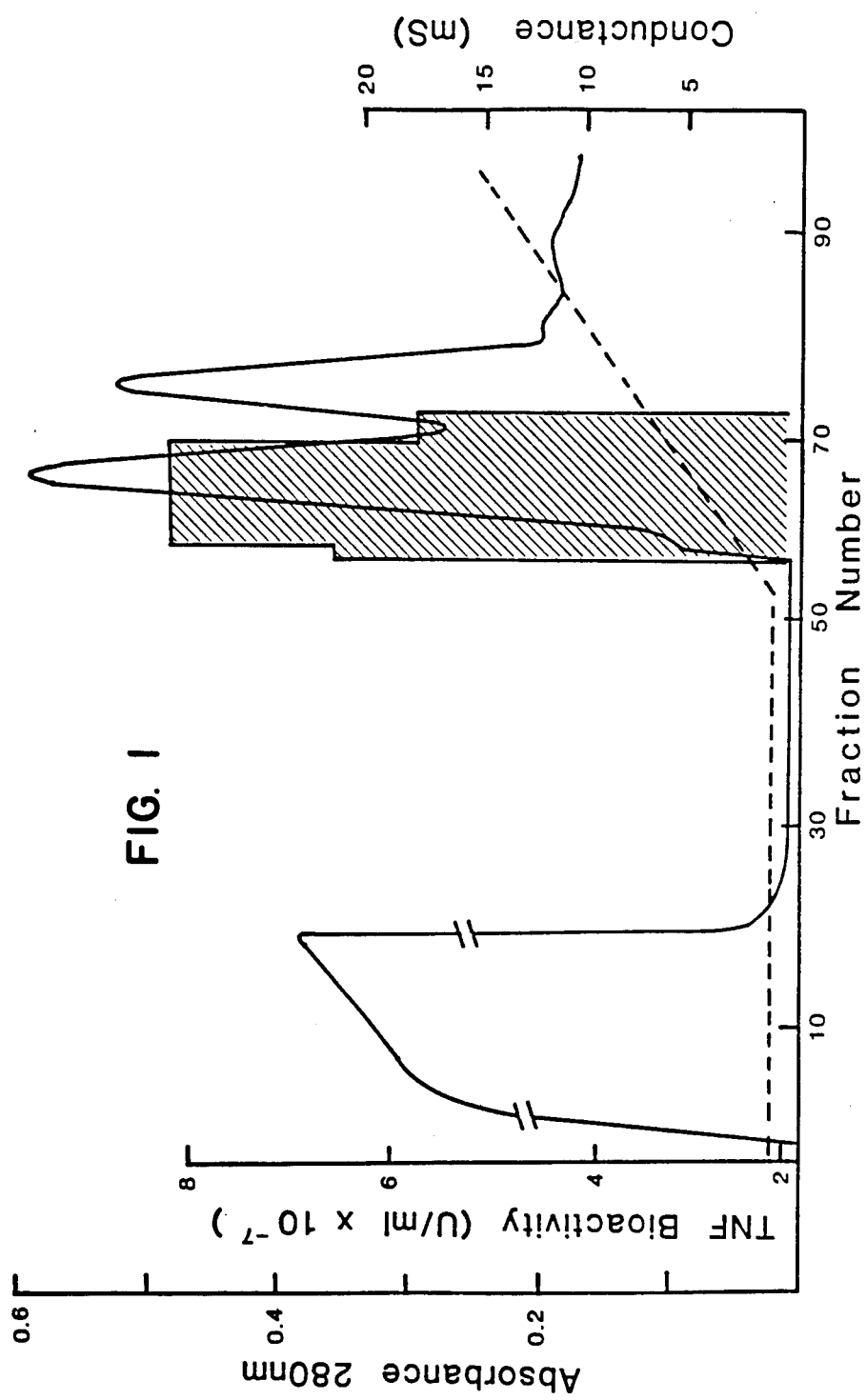
FIG. 1 shows an elution profile from DEAE Sepharose of a crude bacterial extract containing recombinant TNF.

As used herein, "tumor necrosis factor" (TNF) refers to an amino acid sequence substantially equivalent to that shown in FIG. 4, which is capable of selective cytotoxicity against tumor cells. The amino acid sequence, to fit the definition herein, must be active in the in vitro cytotoxicity assay based on the continuous murine connective tissue cell line L-929 as described in U.S. Ser. No. 730,696, filed May 2 1985, assigned to the same assignee and incorporated herein by reference. This activity is confirmed by in vitro cytotoxicity assay aginst human tumor cells-i.e., the cytotoxicity against L-929 appears to generalize to human tumors. In vivo assays can also be used if desired to confirm these results.

The specific nature of TNF protein depends on the pH of its environment, if suspended or in solution, or of its environment when crystallized or precipitated, if a solid, and thus may be in the form of pharmaceutically acceptable salts or may be in neutral form. The free amino groups of the protein are, of course, capable of forming acid addition salts with, for example, inorganic acids such as hydrochloric, phosphoric, or sulfuric acid; or with organic acids such as, for example, acetic, glycolic, succinic, or mandelic acid. The free carboxyl groups are capable of forming salts with bases, including inorganic bases such as sodium, potassium, or calcium hydroxides, and such organic bases as piperidine, glucosamine, trimethylamine, choline, and caffeine. In addition, the protein may be modified by combination with other biological materials such as lipids and saccharides, or by side chain modification such as acetylation of amino groups, phosphorylation of hydroxyl side chains, or oxidation of sulfhydryl groups. The TNF recombinantly produced using bacteria as hosts presumably lacks these additional moieties. All of these modifications are included within the scope of the definition, so long as the TNF activity is retained.

It is also understood that minor modifications of primary amino acid sequence may result in proteins which have substantially equivalent or enhanced activity as compared to the sequence set forth in FIG. 4. These modifications may be deliberate, as through site-directed mutagenesis, or may be accidental such as through mutation in hosts which are TNF producers.

In particular, muteins lacking up to and including the first ten amino acids at the N-terminus of the sequence shown in FIG. 4 have comparable or greater specific activities as compared to the TNF of the structure shown. The pattern of specific activities appears to follow a ball-shaped curve with an optimum activity when 6–8 N-terminal amino acids are deleted. Accordingly, the definition of TNF specifically includes these truncated forms, as clearly, deletions of up to 10 amino acids from the N-terminus do not destroy, but, in fact, sometimes enhance biological activity.

In addition, deletions from the C-terminus of TNF as shown in FIG. 4 are also expected to be harmless. Constructions for genes encoding deletions of up to 17 amino acid residues have been made (see U.S. Ser. No. 760,661, filed July 30 1985, assigned to the same assignee and and incorporated by reference.)

U.S. Ser. No. 698,939, filed Feb. 7 1985, assigned to the herein assignee and incorporated herein by reference, discloses cysteine-depleted muteins of the TNF shown in FIG. 4. In general, neutral amino acid replacements of the cysteine at position 69 result in active TNF proteins. It appears that the cysteine at position 101 is also dispensible, and muteins having alternate neutral amino acids in this position, as well as muteins wherein both cysteines 69 and 101 have been replaced, have been prepared. These muteins can also be modified to obtain truncated forms, for example to lack 1–10 amino acids at the N-terminus, sequences of amino acids at the C-terminus, or both. These muteins also retain TNF activity and may have enhanced biological activity in vitro and in vivo.

As to notation, for convenience, the protein having the amino acid sequence numbered 1–157 in FIG. 4 will be used as a reference and designated, perhaps arbitrarily, mTNF (mature TNF). All other amino acid sequences having homology with mTNF and showing TNF biological activity will be referred to as "muteins" of mTNF and will be denoted as to their differences from mTNF using the numbering of residues shown in the figure. For example, muteins which have substitutions for cysteine at position 69 will be denoted using the substituted residue and the position number, e.g., peptides having a serine in place of the cysteine at position 69 are designated $ser_{69}$ TNF. If a residue is simply missing, it will be renamed as a des-residue, so that, for example, the mutein wherein the serines at positions 3 and 4 are deleted will be designated $des\text{-}ser_3 des\text{-}ser_4$ TNF. Muteins which lack segments of amino acids at the N- or C-terminus are denoted according to the terminus affected. Deletions at the N-terminus will be shown as lacking the appropriate number of amino acids using $\nabla$ followed by the number missing. For example, muteins which lack one N-terminal amino acid as compared to the protein shown in FIG. 1 will be designated $\nabla 1$TNF. For deletions at the C-terminus, the $\nabla$ will be followed by the number of the last remaining residue and a minus sign. Thus for the mutein having 7 amino acids removed from the C-terminus, the designation would be $\nabla 150$-TNF. Where combinations of the foregoing alterations are made, the designation shows all of them, e.g. $\nabla 1 des\text{-}ser_3 des\text{-}ser_4 ser_{69} \nabla 150$-TNF.

Not all muteins of TNF are recombinantly or deliberately produced. Indeed, the sequence obtained for the twenty-two N-terminal amino acids of the HL-60 secreted TNF contains minor modifications in the primary structure although both native and recombinant proteins exhibit TNF activity. Specifically, the recombinant sequence has an additional pair of serine residues preceding the serine at position 5 before resuming the homology between positions 4–12 of the HL-60 derived protein and positions 6–14 of the deduced sequence.

"By chromatography" means that the subject mixture is treated with an adsorbent or other support and then eluted, usually with a gradient or other seqential eluant as opposed to a simple one step process. The sequential elution is most commonly done by placing the support in a column and supplying an eluting solution which changes its character either stepwise or preferably by gradient. However, other methods may be used, such as placing the support in a filter and sequentially administering eluants of differing character. As used herein, "by chromatography" means that this elution must done so as to elute less than all of the materials retained by the support at one time. Thus, if done batchwise, the elution must be accomplished so as to remove only the desired component and leave the remaining materials adhering to the column or must comprise more than one step.

As used herein "mixture" as it relates to mixtures containing TNF refers to a collection of materials which includes TNF but which also includes alternate proteins. If the TNF is derived from recombinant host cells, the other proteins will ordinarily be those associated with the host. Where the host is bacterial, the contaminating proteins will, of course, be bacterial proteins. However, if the TNF is associated with native sources, such proteins will be mammalian. Other non-proteinaceous materials may also be present but generally do not constitute a purification problem.

By "high salt concentration conditions" is meant an aqueous solution wherein an ionic substance is present to create conditions of high ionic strength. Ionic strength is defined as is understood in the art to be calculated from the putative concentrations of the various ions placed in solution modified by their activity coefficients. Workable high salt concentrations are typified by solutions containing high concentrations of ammonium sulfate. However, other salts such as sodium chloride, potassium chloride, sodium sulfate, or sodium nitrate can be used instead, provided solubility permits and provided the same ionic strength can be obtained.

B. General Method and Preferred Embodiments

The general method at the heart of the invention is the application of a mixture containing TNF to a chromatographic column containing hydrophobic particulate support such as phenyl TSK, available from LKB. Hydrophobic supports in general are comprised of alkyl, phenyl, or other essentially hydrocarbyl substituents bound to a matrix, usually a carbohydrate, but other polymers, such as polyacrylamide, are also usable. Other exemplary hydrophobic supports which are usable in the method of the invention include phenyl sepharose, octyl sephrose, and phenyl agarose. However, phenyl TSK is preferred.

In a preferred mode, the mixture containing TNF protein is brought to around 1.5–2M ammonium sulfate, preferably 1.8M ammonium sulfate contained in approximately 0.1M sodium phosphate, approximately pH 7.0. Of course, other buffers maintaining approximately neutral pH could be used.

The TNF protein elutes from a hydrophobic column at a low salt concentration depending on the mutein form chromatographed and on whether analytical or preparative columns are used. As a preliminary matter, it is noted that for analytical columns, ∇4TNF, for example, is still retained when the buffer concentration remains at approximately 0.1M even when the concentration of ammonium sulfate is reduced to zero. However, during the subsequent decreasing ion gradient, when the buffering ions are also deleted from the solution, the ∇4TNF elutes at approximately 0.02M sodium phosphate. Accordingly, ∇4TNF elutes from the hydrophobic analytical support in an ionic strength range corresponding to approximately 0.02M sodium phosphate, an ionic strength that can be mimicked by appropriate concentrations of other salts. On the other hand, mTNF elutes from the phenyl TSK analytical column when the ammonium sulfate concentration is reduced to about 0.4M, and the buffer is still present.

Table 1 shows the conditions for elution of the various TNF muteins from a preparative phenyl TSK support. The results differ from those obtained on an analytical column as is often the case for protein separations. However, the muteins also in this case exhibit different behaviors from each other. Their behavior in preparative column is, of course, of greater relevance to the use of hydrophobic columns in purification.

TABLE 1

| | Phenyl TSK Elution Gradient for Preparative Columns | | |
|---|---|---|---|
| | % TNF Mutein Eluted at | | |
| TNF Mutein | 0.36 M $(NH_4)_2SO_4$ 100 mM $NaP_i$ | 0.0 M $(NH_4)_2SO_4$ 100 mM $NaP_i$ | 0.0 M $(NH_4)_2SO_4$ 20 mM $NaP_i$ |
| mTNF | 80% | 0% | 20% |
| ∇4TNF | 80% | 0% | 20% |
| ∇7TNF | 25%* | 5%* | 70%* |
| ∇6TNF | 50% | 0% | 50% |
| ∇8TNF | 50% | 0% | 50% |
| ∇9TNF | 30% | 0% | 70% |
| ∇10TNF | <1% | 10% | 90% |

*Each sample showed the same IEF pattern, amino acid composition, and N—terminal sequence.

The mixture subjected to the process of the invention is preferably a mixture from bacterial culture wherein the contaminants are bacterial proteins. In a typical such preparation, the bacterial host transformed with vectors encoding recombinant TNF is cultured and induced for TNF production according to the sequences controlling the gene. Typical vectors and means of expression are set forth in detail in U.S. Ser. No. 760,661, as incorporated by reference hereinabove.

The crude extract is prepared, for example, by sonicating the bacterial host expressing the recombinant TNF gene. It is preferred that a preliminary purification of this extract on anion exchange support be performed. The various TNF muteins also show differing elution patterns in anion exchange chromatography. For example, using DEAE cellulose and an increasing NaCl gradient, mTNF was eluted at 40 mM NaCl, ∇4TNF began to elute late in the 40 mM NaCl portion and mainly came off the column at 60 mM, ∇10TNF eluted at 60 mM NaCl, and ∇6-, ∇8-, and ∇9TNF eluted at 80 mM NaCl (both from DEAE cellulose and from Mono Q).

Briefly, the appropriate *E. coli* strain, in the illustrated instances, *E. coli* strain K12 MC1000 lambda lysogen (ATCC 395531) or a similar strain such as DG95, is transformed with a recombinant vector effective in expressing the desired TNF. In the illustrated vectors, all of the gene sequences are under the control of the $P_L$ promoter and the cells are grown at 37° C. under standard growth medium conditions to an $OD_{600}$ of about 0.5 and then induced by increasing the temperature to 42° C. After two hours, the cells are sonicated and the sonicate is verified to contain TNF activity using in vitro cytotoxicity assay employing murine L-929 cells. Of course, alternate expression vectors and alternate hosts could be employed to generate the recombinant TNF. Other bacterial control sequences, such as the tryptophan (trp) promoter system (Goeddel et al, *Nucleic Acids Res* (1980) 8: 4057) or the penicillinase or lactose (lac) promoter systems (Chang, et al *Nature* (1977) 198: 1056) could also be used with appropriate conditions for growth and promoter induction. Other bacterial hosts besides *E. coli* include, for example, various species of Bacillus or Pseudomonas. In addition, eucaryotic microorganisms such as yeast, or cells grown in tissue culture such as Vero, HeLa, or CHO cells, could be used if appropriate vectors are constructed. Such techniques for expression of foreign genes in a variety of hosts are understood in the art.

The desired TNF will be accumulated in the cell or secreted into the medium, depending upon the construction of the expression vector to include or not to include a functional leader sequence. If a signal sequence is included and the TNF is secreted into the medium, the starting material comprises the supernatant after the cellular debris has been removed. If the TNF is accumulated in the cells, the cells are disrupted, such as by sonication or by mechanical means such as a Hughes press to liberate the contents. The cellular extract or harvested supernatant is then used as the initial mixture containing TNF.

In a preferred mode of carrying out the invention, the starting material is first subjected to ion exchange chromatography using, for example, DEAE agarose, DEAE cellulose or QAE agarose, preferably DEAE agarose. The treatment conditions are such that the TNF is retained on the support and can be eluted by increasing ionic strength. Typical conditions are Tris buffer at pH 7–9, preferably around pH 8, and a salt concentration of approximately 1 mM NaCl. Elution is accomplished by increasing the salt concentration in either stepwise or gradient increments to obtain elution of the retained components; TNF elutes under these conditions at approximately 55 mM NaCl. The TNF-containing fractions are determined by subjecting the fractions collected to cytotoxicity or other assay for TNF, and those containing TNF are pooled and subjected to further purification.

In the method of the invention, the TNF-containing mixture, preferably the pooled fractions from the DEAE Sepharose, column is brought to 1.8M ammonium sulfate, or the ionic strength of solution is comparably adjusted with alternate salts in the presence of 0.1M sodium phosphate buffer. The solution is then applied to a chromatographic column containing the hydrophobic support, preferably phenyl TSK support. The TNF is retained under these conditions. The column is the eluted by decreasing the concentration of ammonium sulfate, and finally the concentration of phosphate in the buffer. The process is most efficiently conducted under high performance (HPLC) conditions, but this is a not a requirement. Again, the eluted fractions are tested for TNF activity using any convenient assay such as the cytotoxicity assay used in Ser. No. 760,661 cited above. Those fractions which contain TNF activity may then optionally be further purified by gel filtration with a pore size adjusted according to peculiar size of the contaminants. Any gel filtration resin with a size range between that of S-200 and G-25 may be used to separate the desired TNF from the salts remaining from the hydrophobic chromatography support step.

The resulting TNF preparation is homogeneous by SDS-Page and recoveries are typically 50–80% of total activity.

C. Example

The following example is intended illustrate but not to limit the invention.

E. coli DG95 was transformed with pAW711, a plasmid containing cDNA sequences encoding mature human TNF under the control of $P_L$ promoter. The cells were grown and induced for TNF production before harvesting by centrifugation at 27,000×g for 5 minutes.

The cells were washed with 10 mM Tris buffer, pH 7.0, and disrupted by sonication. The cell debris was removed by centrifugation at 27,000×g for 15 minutes, and the pH of the culture supernatant was adjusted to 8.2 and the salt concentration to 1 mM NaCl.

The supernatant was then applied to a DEAE agarose column which was equilibrated with 10 mM Tris pH 8.2/1 mM NaCl. The column was then eluted with a gradient of 0–1M NaCl and 10 mM Tris, pH 8.2. Fractions were collected and assayed for TNF bioactivity, and for protein content by the method of Lowry.

FIG. 1 shows the elution profile from the DEAE Sepharose column. It is apparent that a portion of the bacterial proteins are not retained by the column and that the TNF activity elutes at a salt concentration level of about 55 mM NaCl.

The fractions from the DEAE column containing TNF activity were pooled and adjusted to 1.8M ammonium sulfate by the addition of the solid salt and applied to a preparative phenyl TSK HPLC column (Toyo-Soda, LKB) previously equilibrated in 1.8M ammonium sulfate/0.1M sodium phosphate buffer pH 7.0. The column was then eluted with a linear gradient of decreasing ammonium sulfate concentration in 0.1M phosphate buffer pH 7.

Figure 2:
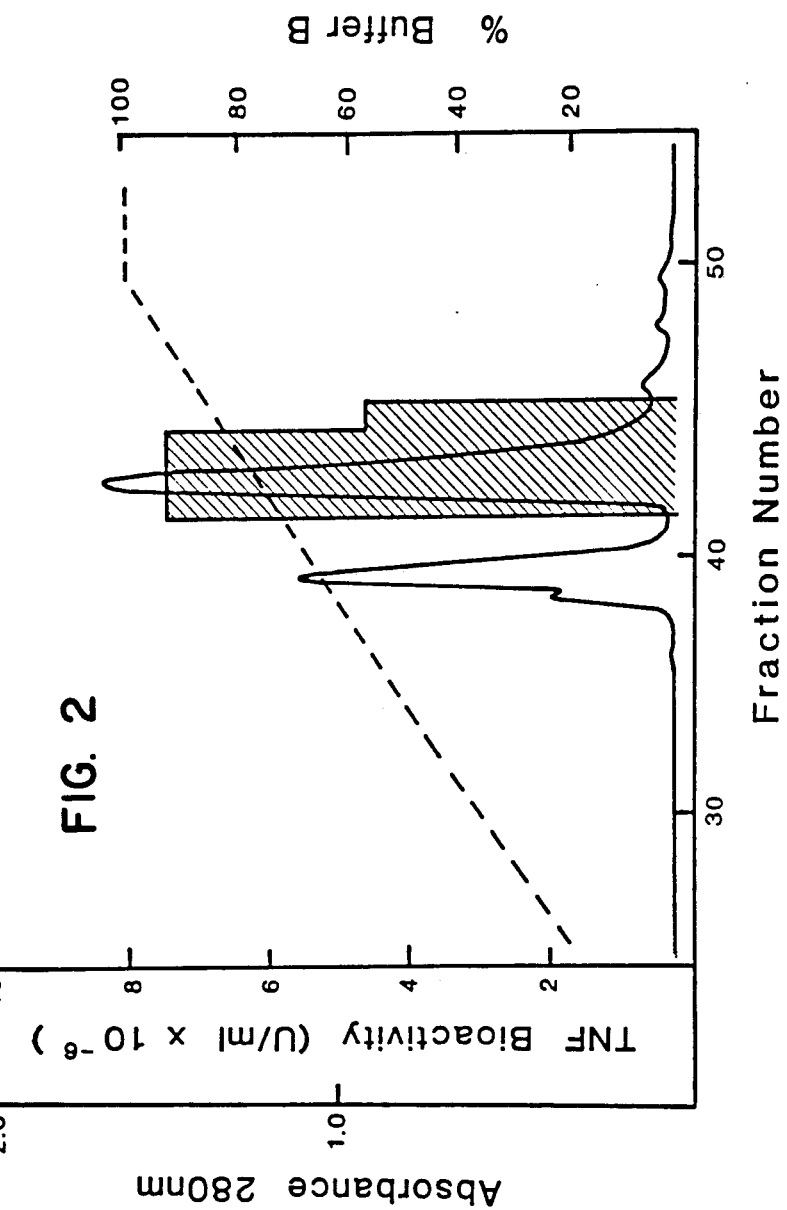
FIG. 2 shows the elution profile of hydrophobic HPLC using a phenyl TSK column, to which TNF has been adsorbed, using a decreasing salt concentration gradient.

FIG. 2 shows the elution profile and the successful separation from a contaminating protein of the TNF-containing fractions. The fractions containing TNF activity were then pooled and chromatographed through GH-25 Cellufine for desalting.

Table 2 below shows the progress of purification in the foregoing procedure. Both the DEAE and the phenyl TSK HPLC columns effect an approximately tenfold increase in specific activity. Total recovery was 30 percent after the gel filtration step.

TABLE 2

| Purification Step | Purification of rTNF | | | |
|---|---|---|---|---|
| | Total Protein (mg) | Units | Specific Activity (U/mg) | % Purity | % Recovery |
| Sonicate supernatant | 60 | $200 \times 10^5$ | $3 \times 10^5$ | 5–8 | 100 |
| DEAE Tris-Acryl (ion exchange) | 2 | $100 \times 10^5$ | $5 \times 10^6$ | 60–80 | 50 |
| Phenyl TSK-HPLC (hydrophobic) | 1.6 | $200 \times 10^5$ | $1.2 \times 10^7$ | >95 | 50 |
| GH-25 Cellufine (desalt) | 0.6 | $60 \times 10^5$ | $1 \times 10^7$ | >95 | 30 |

In a similar manner, E. coli transformed with plasmids encoding various deletion muteins of TNF were cultured and TNF muteins extracted. These extracts were subjected to the foregoing procedure to yield homogeneous proteins of comparable purity.

However, the muteins having N-terminal deletions were eluted at different stages of the decreasing salt gradient. While the mTNF illustrated was eluted at 0.4M ammonium sulfate, ∇7TNF, for example, did not elute for the most part until the ammonium sulfate concentration was reduced to zero and the sodium phosphate to 0.02M (see Table 1 supra).

Figure 3:
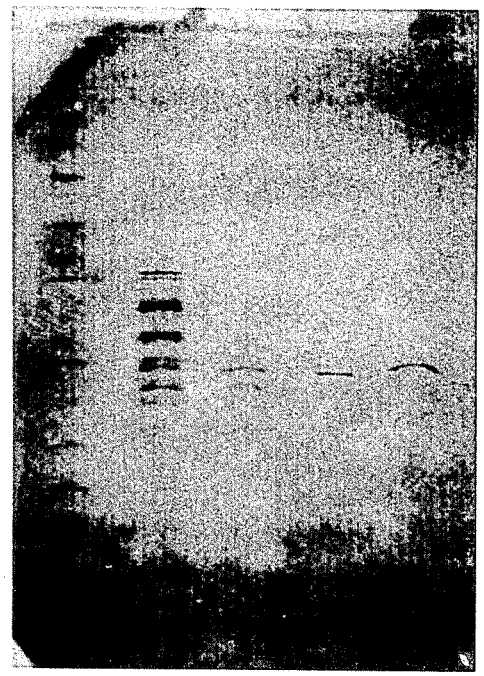
FIG. 3 shows the results of an isoelectric focusing gel perfomed on purified recombinant TNF and muteins thereof.

The purified proteins were subjected to isoelectric focusing with the results shown in FIG. 3. Lane 1 contains molecular weight markers, lane 2 contains mature recombinant TNF; lanes 3–5 contain muteins of TNF which are missing 4 N-terminal, 7 N-terminal, and 6 N-terminal amino acids, respectively. While all proteins were of similar molecular weight in each case, the mature TNF shows a family of proteins of varying pI values, indicating possible side chain modification has occurred. This effect is minimized in the muteins.

The purification procedure as set forth in the example for mTNF can be summarized by the flow chart below:

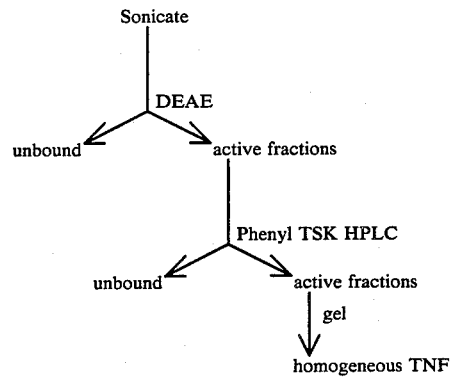

We claim:

1. A method for purifying TNF which comprises the steps of (a) treating an aqueous mixture containing TNF with a hydrophobic interaction chromatographic support comprising hydrocarbyl substituents bound to an uncharged, polymeric, particulate matrix in the presence of an aqueous solution containing a concentration of ions that is effective to result in retention of TNF on the hydrophobic support, but ineffective to precipitate the TNF, and (b) eluting the TNF from the hydrophobic support chromatographically by decreasing the ion concentration below the concentration of ion used in step (a).

2. The method of claim 1 wherein the TNF is recombinant TNF.

3. The method of claim 2 wherein the TNF is an N-terminal deleted mutein.

4. The method of claim 1 wherein the mixture contains bacterial proteins and is free of other mammalian proteins.

5. The method of claim 1 wherein the hydrophobic chromatographic support is phenyl TSK HPLC support.

6. The method of claim 1 wherein the the aqueous solution comprises 1.5–2.0M ammonium sulfate and 0.1M sodium phosphate, pH 7.

7. The method of claim 6 wherein the the aqueous solution comprises 1.8M ammonium sulfate and 0.1M sodium phosphate, pH 7.

8. The method of claim 1 wherein the steps are carried out as HPLC.

9. The method of claim 1 wherein the decrease in ion concentration is by continuous gradient.

10. The method of claim 1 wherein the mixture has previously been enriched in TNF by ion exchange chromatography.

11. The method of claim 1 which further includes treating the eluted TNF with a sizing gel.

12. A method for purifying TNF which comprises the steps of (a) eluting unpurified TNF from an anion exchange support matrix in the presence of a concentration of ions which is effective to elute an aqueous mixture containing TNF from the support matrix but not to precipitate TNF from aqueous solution, (b) without a desalting step, treating the eluted aqueous mixture containing TNF with a hydrophobic interaction chromatographic support comprising hydrocarbyl substituents bound to an uncharged, polymeric, particulate matrix in the presence of an aqueous solution containing a concentration of ions that is effective to result in retention of TNF on the hydrophobic support, but ineffective to precipitate the TNF, and (c) eluting the TNF from the hydrophobic support chromatographically by decreasing the ion concentration below that effective for TNF retention.

* * * * *